(12) United States Patent
Kagan et al.

(10) Patent No.: US 6,193,133 B1
(45) Date of Patent: Feb. 27, 2001

(54) METHOD AND ARTICLES FOR EVALUATING WELDED JOINTS

(75) Inventors: Val A. Kagan, Morris Plains, NJ (US); Chul S. Lee, Northville, MI (US)

(73) Assignee: AlliedSignal Inc., Morristown, NJ (US)

( * ) Notice: Subject to any disclaimer, the term of this patent is extended or adjusted under 35 U.S.C. 154(b) by 0 days.

(21) Appl. No.: 09/443,595

(22) Filed: Nov. 19, 1999

(51) Int. Cl.[7] .............................. B23K 31/12; G01N 3/20

(52) U.S. Cl. ................................ 228/103; 29/705; 73/850

(58) Field of Search .............................. 228/103; 29/705; 73/850

(56) References Cited

U.S. PATENT DOCUMENTS

| | | | |
|---|---|---|---|
| 3,892,089 | * | 7/1975 | Coulstring ............................ 51/34 D |
| 4,365,132 | * | 12/1982 | Kazlauskas et al. ............... 219/60 A |
| 4,899,923 | * | 2/1990 | Findlan ............................... 228/193 |
| 5,024,343 | * | 6/1991 | Lemelson ............................ 220/326 |
| 5,415,047 | * | 5/1995 | Maciejewski et al. ................ 73/850 |
| 5,528,942 | * | 6/1996 | Baratta ................................. 73/856 |
| 5,738,268 | * | 4/1998 | VanderPol et al. .................. 228/103 |
| 5,802,903 | * | 9/1998 | Nakajima ............................. 72/224 |
| 6,039,307 | * | 3/2000 | De Zen ................................ 256/19 |

FOREIGN PATENT DOCUMENTS

| | | | |
|---|---|---|---|
| 363242477 | * | 10/1988 | (JP) ................................. 219/121.12 |
| 06291744 | * | 10/1994 | (JP) ................................. 219/121.11 |
| 355036072 | * | 10/1994 | (JP) ................................. 219/121.11 |
| 406297144 | * | 10/1994 | (JP) ................................. 219/121.11 |

OTHER PUBLICATIONS

H. Rajaraman, et al., The Effect of Glass Fiber Fillers on the Welding Behavior of Poly P–Phenylene Sulfide, ANTEC: 896–899 (1992).

M. J. Behnfeldt, et al., Variable–frequency technique for vibration welding of plastics parts, Plastics Machinery & Equipment (May 1978).

V. K. Stokes, Analysis of the friction (spin)–welding process for thermoplastics, *J. Mat. Sci.*: 2772–2785 (1988).

Friction Welding of Plastics, Welding in the World, vol. 16 No. 11/12 (1978).

E.D. Nicholas, Friction Welding Plastics, The Welding Institute Research Bulletin, (UK), Res. Bull. 17 211 (Aug. 1976).

R. J. Crawford, et al., Friction Welding of Plastics, *J. Mat. Sci.* 16(12): 3275–82 (1981).

H. Potente, et al., Vibration Welding of High Temperature Plastics, ANTEC: 2075–81 (1993).

H. Potente, et al., Process Data Acquisition in Vibration Welding of Thermoplastics, ANTEC: 464–469 (1989).

H. Potente, et al., The Effects of Moisture in the Vibration Welding of Polyamide, ANTEC: 1320–26 (1994).

V. K. Stokes, et al., Strength and Bonding Mechanisms in Vibration–Welded Polycarbonate to Polyetherimide Joints, ANTEC: 470–473 (1989).

V. K. Stokes, Cross–Thickness Vibration Welding of Thermoplastics, ANTEC: 880–883 (1992).

V. K. Stokes, Vibration Welding of Thermoplastics. Part I: Phenomenology of the Welding Process, *Polymer Engineering and Science*, vol. 28, No. 11: 718–727 (1988).

(List continued on next page.)

Primary Examiner—Patrick Ryan
Assistant Examiner—L. Edmondson
(74) *Attorney, Agent, or Firm*—Roger H. Criss

(57) ABSTRACT

Two polygon shaped articles having walls of different thicknesses are mated and welded together. Specimens cut from this composite part are used to evaluate the performance of welded joints with the influence of design, processing conditions such as welding, molding, and the like, and material composition. The evaluation advantageously provides an accurate predictor for linear vibration, orbital vibration, hot plate, hot gas, hot gas extrusion and infrared welding at a variety of bead thicknesses.

10 Claims, 5 Drawing Sheets

OTHER PUBLICATIONS

V. K. Stokes, Vibration Welding of Thermoplastics. Part II: Analysis of the Welding Process, *Polymer Engineering and Science*, vol. 28, No. 11: 728–739 (1988).

V. K. Stokes, Vibration Welding of Thermoplastics. Part III: Strength of Polycarbonate Butt Welds, *Polymer Engineering and Science*, vol. 28, No. 15: 989–997 (1988).

V. K. Stokes, Vibration Welding of Thermoplastics. Part IV: Strength of Poly(Butylene Terephthalate), Polyetherimide, and Modified Polyphenylene Oxide Butt Welds, *Polymer Engineering and Science*, vol. 28, No. 15: 998–1008 (1988).

V. K. Stokes, Thickness Effects in the Vibration Welding of Polycarbonate, ANTEC: 479–481 (1989).

N. S. Taylor, The Vibration Welding of Thermoplastic Extruded Sheet: *An Exploratory Study*, 7004.02/87/569.2: 1–15.

A. K. Schlaeb, et al., The Impact Strength of Butt Welded Vibration Welds Related to Microstructure and Welding History, *Polymer Engineering and Science*, vol. 29, No. 23: 1677–1682 (1989).

S.M. Tavakoli, Effects of ageing on tensile properties and structure of linear friction and hot plate welds in polyethersulphone, TWI Technology Briefing 481/1993 (1993).

D. A. Grewell, An Application Comparison of Orbital and Linear Vibration Welding of Thermoplastics, Society of Plastic Engineers, (New York), ANTEC (1999).

V. A. Kagan, Collection of Related Articles, Papers and Patents, Welding and Engineering Properties of Thermoplastics, Honeywell (1999).

\* cited by examiner

METHOD AND ARTICLES FOR EVALUATING WELDED JOINTS

BACKGROUND OF THE INVENTION

1. Field of the Invention

The present invention relates to a method and apparatus for evaluating performance of welded joints.

2. Description of the Prior Art

An evaluation of the performance of welded butt joints has been accomplished by use of standard tensile specimens (ISO or ASTM), rectangular plaques and T-shape elements (ultrasonic welding specimens, American Welding Society G1.2). After welding, the effectiveness of the joints is tested using standard test practices. The use of standard tensile specimens (ISO or ASTM), rectangular plaques and T-shape elements has advantages, among which are the availability of injection-molded plaques, and convenient configuration and size of test specimens for easy machining operations for the specimen preparations. A problem encountered with use of standard tensile specimens (ISO or ASTM), rectangular plaques and T-shape elements is the limitation that these specimens may only be successfully welded using specially prepared, small welding machines. Only one such small size linear vibration welding machine is available commercially at this time. Such a machine, designated Model M-102, is manufactured by Branson Ultrsonic, Germany. When a company is equipped with a mid or large welding machine for welding midsize and large parts, such as lawn mower housings and air intake manifolds, it is very hard to evaluate tensile properties of the joints following the ASTM or ISO procedures. In such circumstances, these specimens are too small for the machine size, and the clamp pressure will be too high. Mechanical performance of thus-welded specimens will often not represent true weld strength property of the material being evaluated.

It would be desirable to provide a method and articles for evaluating welded joints which would overcome the above mentioned shortcomings.

SUMMARY OF THE INVENTION

The invention provides articles and methods for evaluating the performance of welded joints with the influence of design, processing conditions such as welding, molding and the like, and material composition. Advantageously, the invention can be used to perform and evaluate linear vibration, orbital vibration, hot plate, infrared, hot gas, hot gas extrusion welding process, at a variety of bead thicknesses. In practice, two polygon shaped articles having walls of different thicknesses are mated and welded together. Specimens are then cut from this composite part for testing.

More specifically, the invention provides an article for evaluating the performance of welded butt joints and optimizing the design, processing conditions and material composition thereof, comprising: a base plate having a top face and a bottom face; a first polygon shaped welding edge; a second polygon shaped welding edge (hereinafter referred to as "edge"); and a plurality of sets of two parallel walls, each set of walls being provided with a top edge and bottom edge, the top edge and the bottom edge having a predetermined thickness, each wall of a set being oppositely positioned perpendicular to and around the base plate, thereby forming a deep bowl on the top face and a shallow bowl on the bottom face; whereby the top edges form the first polygon shaped edge, and the bottom edges form the second polygon shaped edge.

Preferably, the set of walls has a unique thickness for the top and bottom edges. The plurality of sets of two parallel walls forms an octagon comprised of thermoplastic material. Optionally, the article further comprises a plurality of radial ribs that provide and maintain flexural support for the walls of the deep bowl during welding operations.

The invention also provides a composite welded part for evaluating the performance of thermoplastic welded butt joints and optimizing the design, processing conditions and material composition thereof comprising: a first article and a second article; wherein both the first and second articles comprise a base plate having a top face and a bottom face; a first polygon shaped welding edge; a second polygon shaped welding edge (hereinafter referred to as "edge"); and a plurality of sets of two parallel walls, each set of walls being provided with a top edge and bottom edge, the top edge and the bottom edge having a predetermined thickness, each wall of a set being oppositely positioned perpendicular to and around the base plate, thereby forming a deep bowl on the top face and a shallow bowl on the bottom face; whereby the top edges form the first polygon shaped edge, and the bottom edges form the second polygon shaped edge; and wherein the first article and the second article are mated to each other by welding of their respective polygonal welding edges.

The invention further provides a method for evaluating the strength and life, i.e. creep and fatigue, of welded butt joints, comprising the steps of: selecting a material to be used in forming the butt joints; forming from the material, a first article and a second article, each of the first and second articles having a structure comprising: a base plate having a top face and a bottom face; a first polygon shaped welding edge; a second polygon shaped welding edge (hereinafter referred to as "edge"); and a plurality of sets of two parallel walls, each set of walls being provided with a top edge and bottom edge, the top edge and the bottom edge having a predetermined thickness, each wall of a set being oppositely positioned perpendicular to and around the base plate, thereby forming a deep bowl on the top face and a shallow bowl on the bottom face; whereby the top edges form the first polygon shaped edge, and the bottom edges form the second polygon shaped edge; selecting a first polygon shaped edge of the first article; selecting a first polygon shaped edge of the second article; selecting a set of walls of the first article; selecting a set of walls of the second article; connecting the selected polygon shaped edges and aligning the selected set of walls to mate the first article and the second article together; placing the mated first and second article onto a welding machine; welding the first article to the second article to form a composite part; cutting specimens from the welded selected set of walls of the composite part; and testing the specimens.

The invention represents a significant improvement over previous welding and test systems because it makes possible the evaluation of butt joints for midsize and large parts fabricated in large welding machines. Advantageously, the size and configuration of the article tested is more closely matched with parameters of articles employed in actual manufacturing situations from small to large.

BRIEF DESCRIPTION OF THE DRAWINGS

The invention will be more fully understood and further advantages will become apparent when reference is had to the following detailed description of the preferred embodiments of the invention and the accompanying drawings, wherein like reference numeral denote similar elements throughout the several views and in which.

DESCRIPTION OF THE PREFERRED EMBODIMENTS

The invention provides a method for design, process and material optimization, and evaluating the performance of welded butt joints and an article especially suited for use with the method. In general, the invention can be used to perform and evaluate linear vibration, orbital vibration, hot plate, infrared, hot gas, hot gas extrusion welding at a variety of bead thicknesses. During practice of the invention, two polygon shaped articles having walls of different thicknesses are mated and welded together. Specimens are then cut from this composite part for testing.

Figure 1:
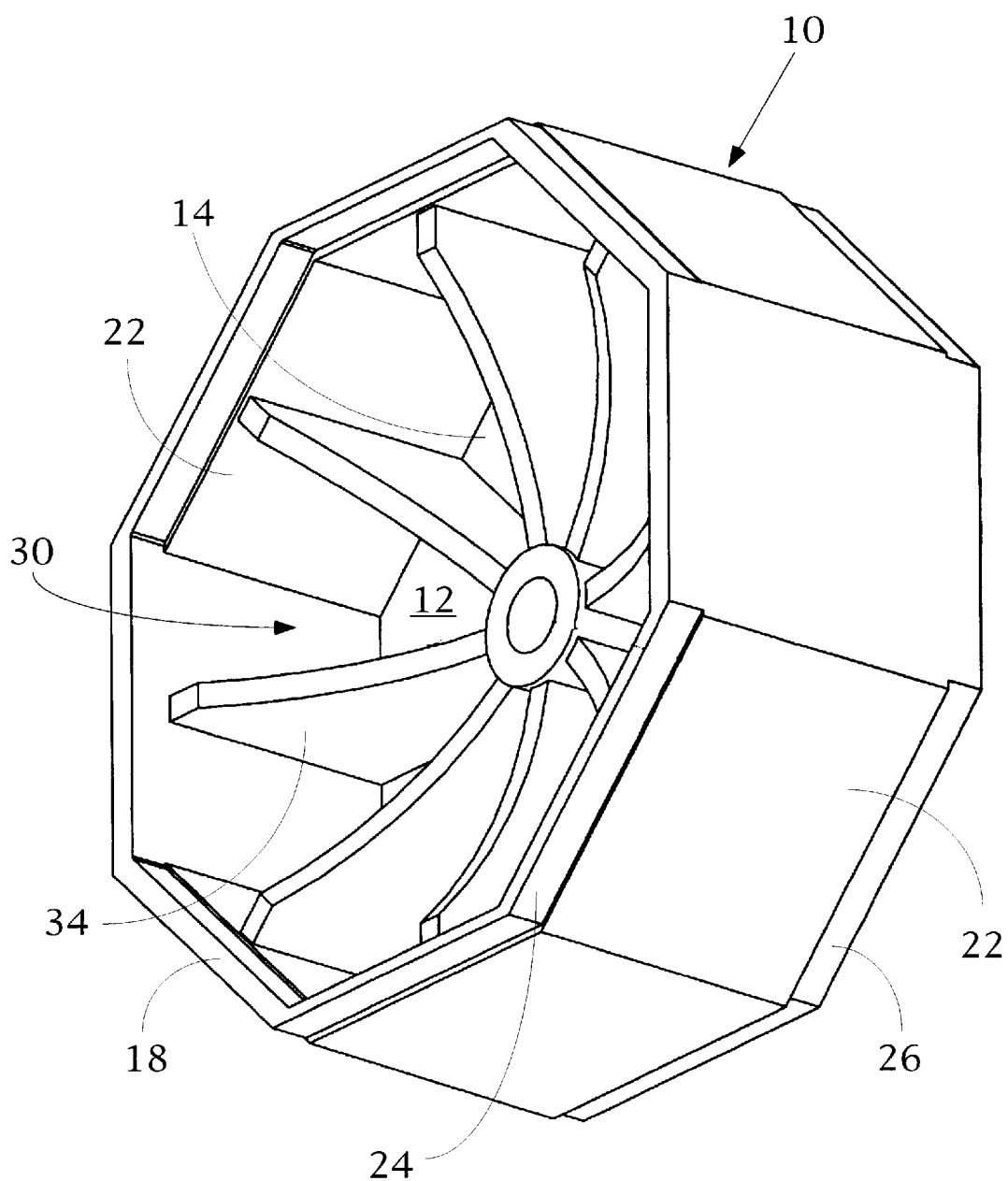
FIG. 1 is a perspective view of the deep bowl side of an article of the invention.
Figure 2:
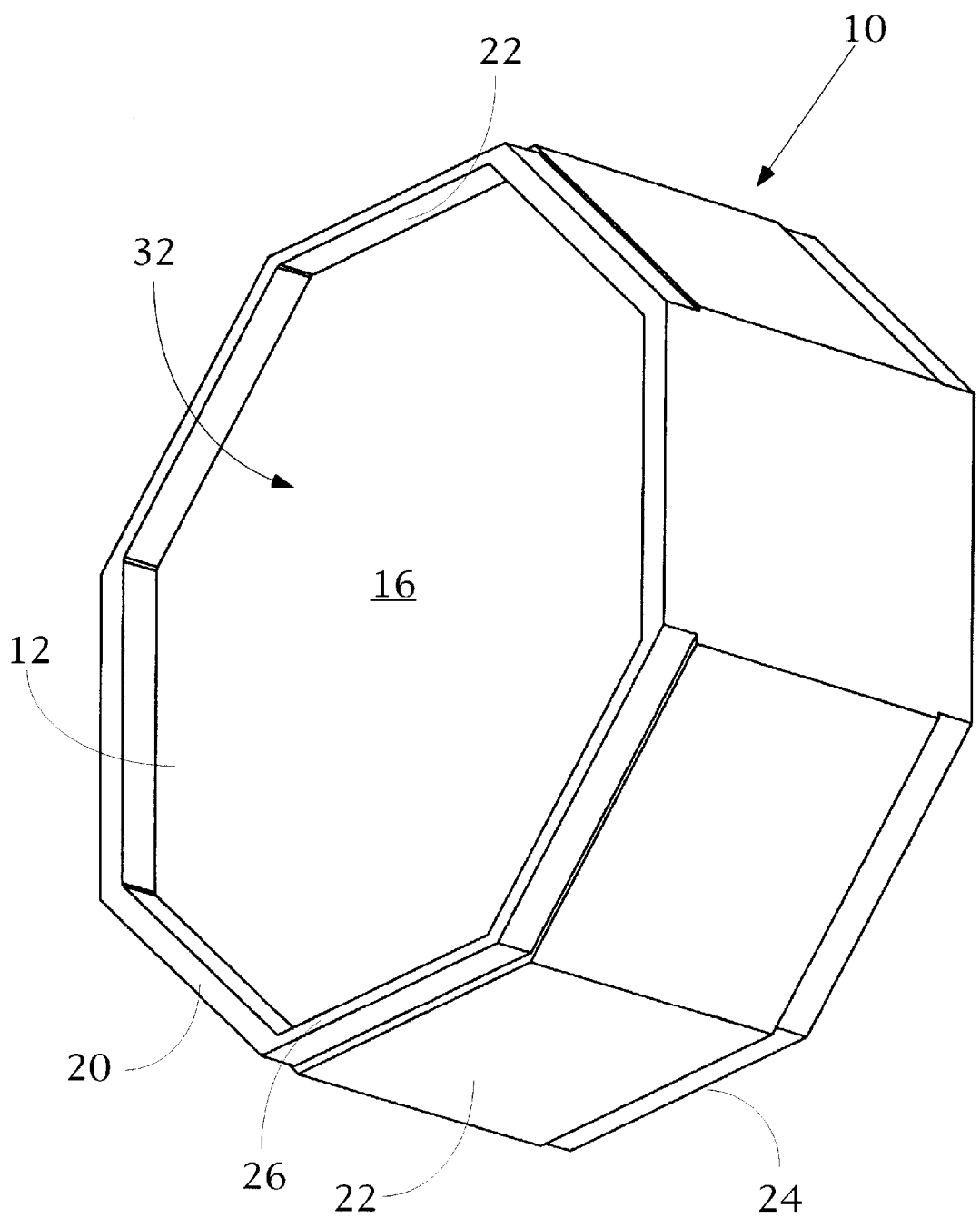
FIG. 2 is a perspective view of the shallow bowl side of an article of the invention.

Referring to FIGS. 1 and 2 of the drawings, there is shown an article 10 for evaluating the performance of welded butt joints. Generally stated, article 10 comprises: a base plate 12 having a top face 14 and a bottom face 16; a first polygon shaped edge 18; a second polygon shaped edge 20; and a plurality of sets of two parallel walls 22, each set of walls being provided with a top edge 24 and bottom edge 26. The top edge 24 and the bottom edge 26 have a predetermined thickness. Each wall of a set is oppositely positioned perpendicular to and around base plate 12, thereby forming a deep bowl 30 on top face 14, and a shallow bowl 32 on bottom face 16. With this arrangement, the top edges form the first polygon shaped edge 18, and the bottom edges form the second polygon shaped edge 20.

The two walls of each set are placed parallel and opposite to each other across base plate 12. Deep bowl 30 is formed on top face 14 of base plate 12, while shallow bowl 32 is formed on bottom face 16 of base plate 12. First polygon shaped edge 18 forms the lip around deep bowl 30, while second polygon shaped edge 20 forms the lip around shallow bowl 32.

Preferably, each set of walls has a unique thickness for top edge 24 and bottom edge 26. As a further preference, there are four sets of two parallel walls, yielding an octagonal form. The thickness of the top edge and bottom edge can be of any selected size. For the octagonal shape, in one embodiment, the four sets of walls have edge thickness values of 2.5 mm, 4.0 mm, 5.0 mm, and 6 mm. In one embodiment, the length of an edge is chosen to result in a weld area of approximately 3,600 mm$^2$.

Optionally, article 10 further comprises a plurality of radial ribs 34, for providing and maintaining flexural support for the walls of deep bowl 30. The composition of the material from which the article is formed, may be of any weldable material. Article 10 is particularly adapted to be formed of a thermoplastic material such as nylon.

Article 10 may be made or designed to form constant height radial ribs, which can also be used for the welding study, on the influence of the fiber orientation effects for fiber filled materials.

Figure 3:
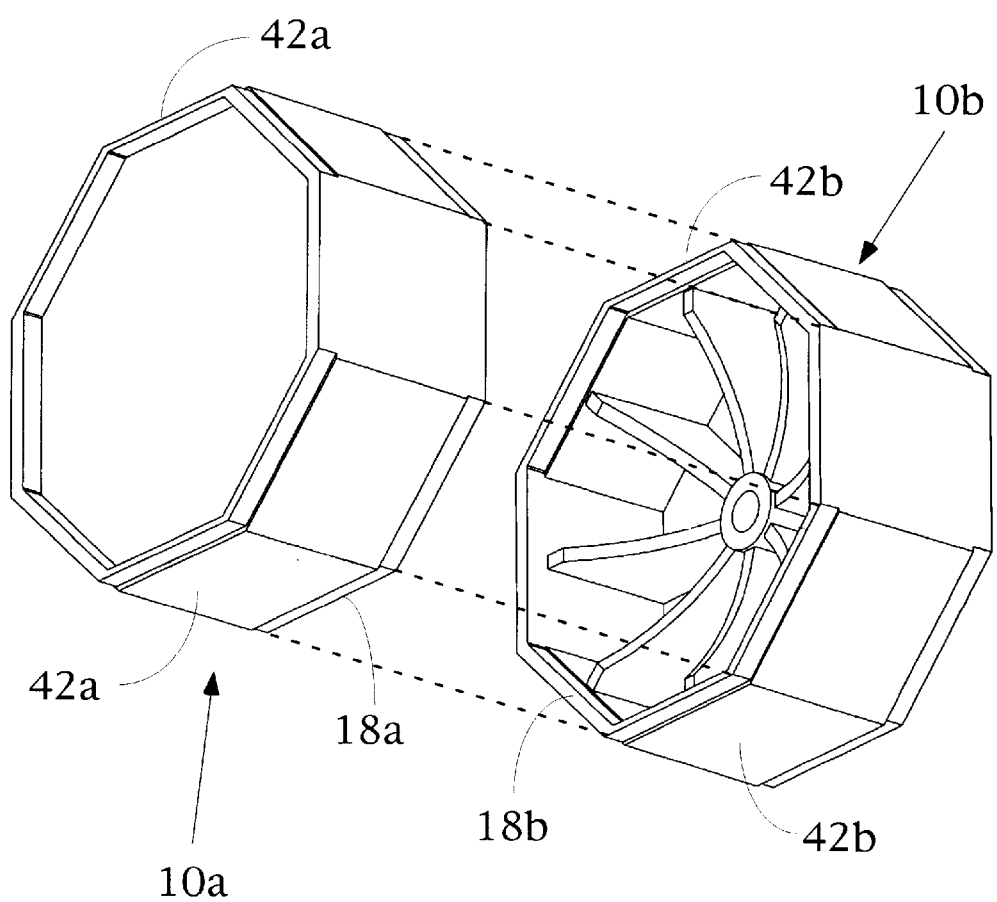
FIG. 3 is a perspective view of a deep bowl to deep bowl alignment of two articles of the invention.
Figure 4A:
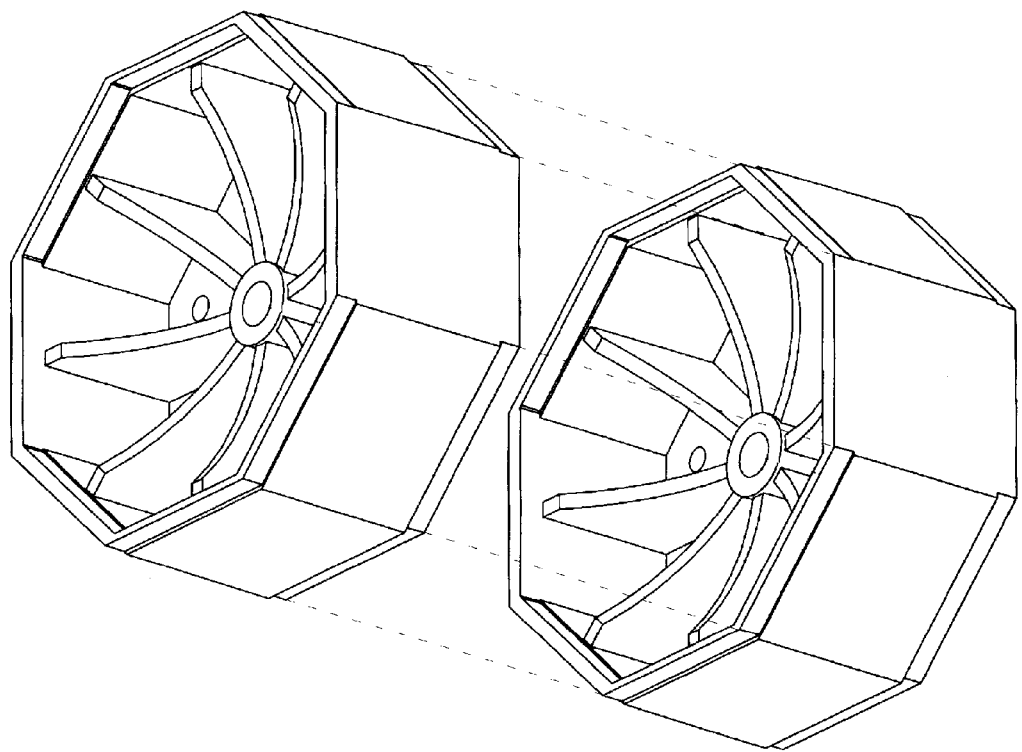
FIG. 4 is a perspective view of two alternative mating configurations.
Figure 4B:
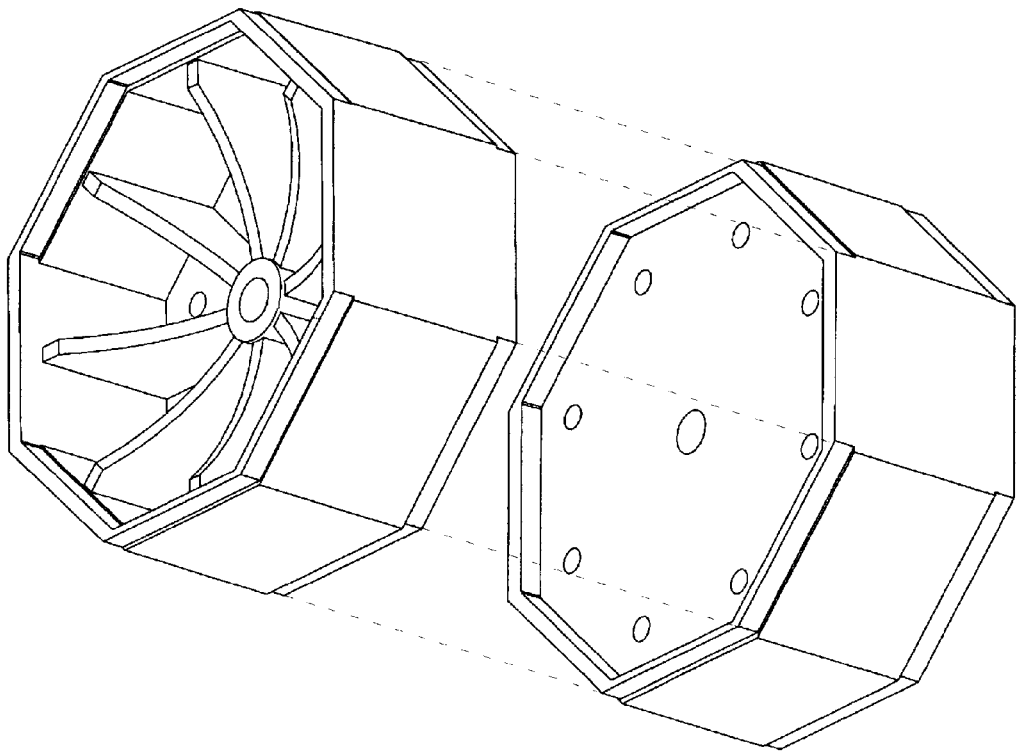
Figure 5:
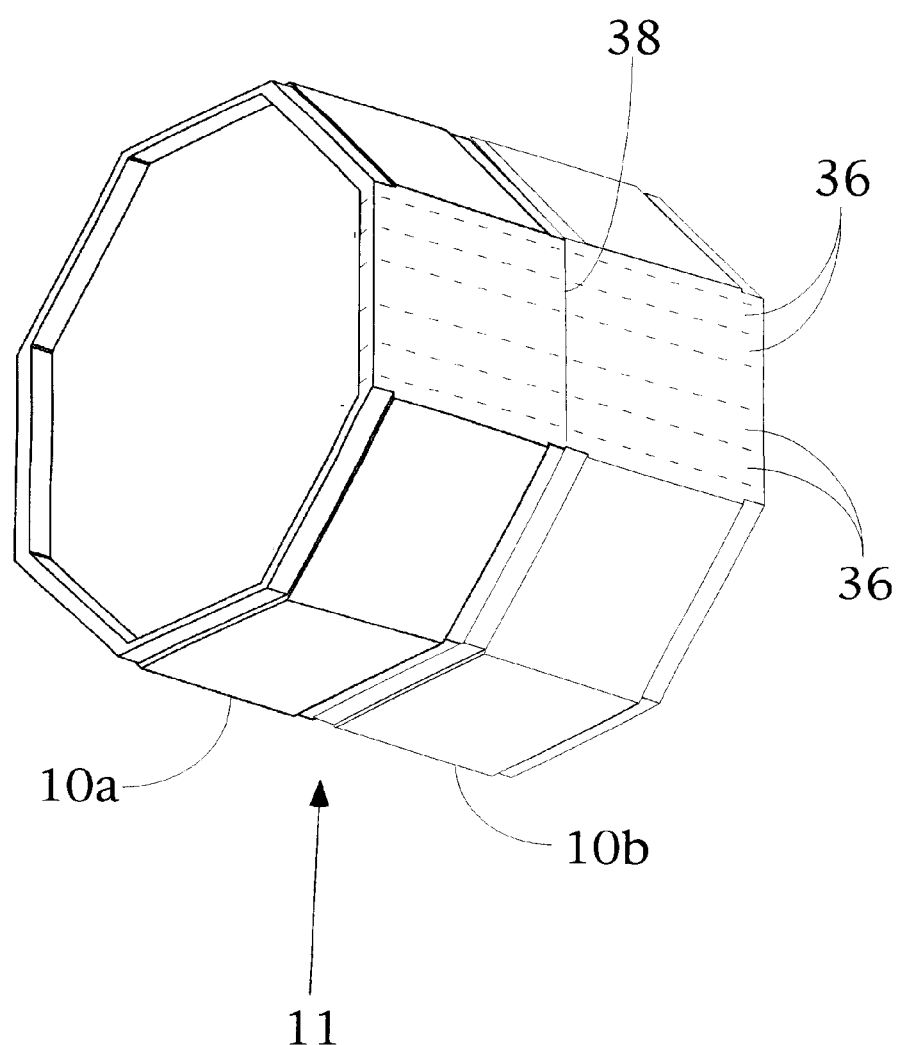
FIG. 5 is a perspective view of a composite part of the invention and specimen cutouts.

In practice, two articles, shown in FIG. 3 as 10a and 10b, are welded together into composite part 11. A set of walls 42 is selected on each article having the desired edge thickness to be tested. Thereafter, the desired configuration is selected. FIG. 3 shows a deep bowl to deep bowl configuration. Alternate configurations include shallow bowl to deep bowl, shown as FIG. 4a, or shallow bowl to shallow bowl, shown in FIG. 4b. In the example shown by FIG. 3, first polygon shaped edge 18a of first article 10a is mated to first polygon edge 18b of second article 10b. As shown by FIG. 5, specimens 36 which encompass welded butt joints 38 are cut from the composite part 11. The composite parts of the invention 11 include as separate embodiments the deep bowl-to-deep bowl welded assembly as in FIG. 3, the shallow bowl-to-deep bowl welded assembly as in FIG. 4a and the shallow bowl-to-shallow bowl welded assembly as in FIG. 4b.

The two articles 10a and 10b are positioned as to the selected configuration, and the selected edge thicknesses are aligned. The mated articles are placed on a welding machine. After welding, specimens 36 are cut from composite part 11 and undergo standard performance testing.

The invention further provides a method for evaluating the strength of vibration welded butt joints, comprising the steps of: selecting a material to be used in forming the butt joints 38; forming from the material a first article 10a and second article 10b; selecting a first polygon shaped edge 18a of first article 10a; selecting a first polygon shaped edge 18b of second article 10b; selecting a set of walls 42a from first article 10a; selecting a set of walls 42b from second article 10b; connecting the selected polygon shaped edges 18a and 18b and aligning selected set of walls 42a and 42b to mate first article 10a and the second article 10b together; selecting an orientation of the selected set of walls with respect to the vibration movement direction of the welding machine; placing the mated first and second article onto a welding machine at the selected orientation; welding first article 10a to second article 10b to form a composite part 11; cutting specimens 36 from the welded selected set of walls of the composite part 11; and testing the specimens. In this manner, the selected set of walls is selected from a plurality of mating joint combinations allowed by the polygon. In addition, a plurality of welded butt joints at a plurality of angles with respect to the vibration movement are produced.

In an alternative embodiment of the invention, the foregoing method is modified by mating shallow bowl to shallow bowl instead of deep bowl to deep bowl. In a further embodiment, the foregoing method is modified by mating deep bowl to shallow bowl instead of deep bowl to deep bowl.

It will be understood by those skilled in the art that a plurality of mating joint thickness combinations can be derived by rotating the two polygon bodies at varying angles with respect to each other, thereby producing additional multiples of mating joint thicknesses. A further feature of the method and article herein described provides means for evaluating vibration weld strength as a function of orientation with respect to the welding movement direction.

In a further embodiment, the composite part described is hot welded. In this embodiment, the method for evaluating the strength of vibration welded joints does not require the step of: selecting an orientation of the selected set of walls with respect to the vibration movement direction of the welding machine. Nor does the method require the step of: placing the mated first and second article onto a welding machine at the selected orientation. The mated first and second article may be placed on the welding machine without attention to orientation since, unlike vibration welding, orientation of a joint appointed for hot welding is not critical.

Having thus described the invention in rather full detail, it will be understood that such detail need not be strictly adhered to but that various changes and modifications may suggest themselves to one skilled in the art, all falling within the scope of the present invention as defined by the subjoined claims.

What is claimed is:

1. An article for evaluating the performance of welded joints and optimizing the design, processing conditions and material composition thereof, comprising:
   a) a base plate having a top face and a bottom face;
   b) a first polygon shaped edge;
   c) a second polygon shaped edge; and
   d) a plurality of sets of two parallel walls, each set of walls being provided with a top edge and bottom edge, said top edge and said bottom edge having predetermined thicknesses, each wall of a set being oppositely positioned perpendicular to and around said base plate, thereby forming a deep bowl on said top face and a shallow bowl on said bottom face;
   whereby said top edges form said first polygon shaped edge, and said bottom edges form said second polygon shaped edge; and
   wherein each of said sets has a unique thickness for said top and bottom edges.

2. An article as recited by claim 1, wherein said plurality of sets of two parallel walls forms an octagon.

3. An article as recited by claim 1, wherein said article is molded from a thermoplastic material.

4. An article as recited by claim 1, further comprising a plurality of radial ribs, said ribs providing and maintaining flexural support for said walls of said deep bowl.

5. A method for evaluating the performance of vibration welded joints, comprising the steps of:
   a) selecting and optimizing a material to be used in forming said butt joints;
   b) forming from said material, a first article and a second article, each of said first and second articles having a construction comprising:
      i.) a base plate having a top face and a bottom face;
      ii) a first polygon shaped edge;
      iii) a second polygon shaped edge;
      iv) a plurality of sets of two parallel walls, each set of walls being provided with a top edge and bottom edge, said top edge and said bottom edge having predetermined thicknesses, each wall of a set being oppositely positioned perpendicular to and around said base plate, thereby forming a deep bowl on said top face and a shallow bowl on said bottom face;
      whereby said top edges form said first polygon shaped edge, said bottom edges form said second polygon shaped edge, and each of said sets has a unique thickness for said top and bottom edges;
   c) selecting a polygon shaped edge of said first article;
   d) selecting a polygon shaped edge of said second article;
   e) selecting a set of walls of said first article;
   f) selecting a set of walls of said second article, said selected set of walls being selected from a plurality of mating joint combinations;
   g) connecting said selected polygon shaped edges and aligning said selected set of walls to mate said first article and said second article together such that each of said sets has a unique thickness for said top and bottom edges;
   h) selecting an orientation of said selected set of walls with respect to the welding movement direction;
   i) placing said mated first and second article at said selected orientation onto a welding machine;
   j) welding said first article to said second article to form a composite part to thereby produce a plurality of welded but joints at a plurality of angles;
   k) cutting specimens from said welded selected set of walls of said composite part; and
   l) testing said specimens.

6. A method for evaluating the performance of welded joints, comprising the steps of:
   a) selecting and optimizing a material to be used in forming said butt joints;
   b) forming from said material, a first article and a second article, each of said first and second articles having a construction comprising;
      i) a base plate having a top face and a bottom face;
      ii) a first polygon shaped edge;
      iii) a second polygon shaped edge;
      iv) a plurality of sets of two parallel walls, each set of walls being provided with a top edge and bottom edge, said top edge and said bottom edge having predetermined thicknesses, each wall of a set being oppositely positioned perpendicular to and around said base plate, thereby forming a deep bowl on said top face and a shallow bowl on said bottom face;
      whereby said top edges form said first polygon shaped edge, and said bottom edges form said second polygon shaped edge, and each of said sets has a unique thickness for said top and bottom edges; and
   c) selecting a polygon shaped edge of said first article;
   d) selecting a polygon shaped edge of said second article;
   e) selecting a set of walls of said first article;
   f) selecting a set of walls of said second article, said selected set of walls being selected from a plurality of mating joint combinations;
   g) connecting said selected polygon shaped edges and aligning said selected set of walls to mate said first article and said second article together such that each of said sets has a unique thickness for said top and bottom edges;
   h) fixing said mated first and second article onto a welding machine;
   i) welding said first article to said second article to form a composite part;
   j) cutting specimens from said welded selected set of walls of said composite part; and
   k) testing said specimens.

7. A composite welded part for evaluating the performance of welded butt joints and optimizing the design, processing conditions and material composition thereof comprising: a first article and a second article; wherein both the first and second articles comprise:
   a) a base plate having a top face and a bottom face;
   b) a first polygon shaped welding edge;
   c) a second polygon shaped welding edge (hereinafter referred to as "edge");
   d) a plurality of sets of two parallel walls, each set of walls being provided with a top edge and bottom edge, the top edge and the bottom edge having a predetermined thickness, each wall of a set being oppositely positioned perpendicular to and around the base plate, thereby forming a deep bowl on the top face and a shallow bowl on the bottom face;
   whereby the top edges form the first polygon shaped edge, and the bottom edges form the second polygon shaped edge, and each of said sets has a unique thickness for said top and bottom edges; and wherein the first article and the second article are mated to each other by welding of their respective polygonal welding edges.

8. A composite part as recited by claim 7 wherein the alignment of the first article and the second article before welding is as shown in FIG. 3.

9. A composite part as recited by claim 7 wherein the alignment of the first article and the second article before welding is as shown in FIG. 4a.

10. A composite part as recited by claim 7 wherein the alignment of the first article and the second article before welding is as shown in FIG. 4b.

* * * * *